United States Patent
Das

[19]

[11] Patent Number: 6,077,281
[45] Date of Patent: *Jun. 20, 2000

[54] SEPTAL DEFECT CLOSURE DEVICE

[75] Inventor: Gladwin S. Das, Lauderdale, Minn.

[73] Assignee: Regents of the University of Minnesota, Minneapolis, Minn.

[*] Notice: This patent is subject to a terminal disclaimer.

[21] Appl. No.: 09/271,762

[22] Filed: Apr. 22, 1999

Related U.S. Application Data

[62] Division of application No. 08/756,776, Nov. 26, 1996, which is a division of application No. 08/284,766, Aug. 2, 1994, Pat. No. 5,578,045, which is a division of application No. 08/062,095, May 14, 1993, Pat. No. 5,334,217, which is a division of application No. 07/822,951, Jan. 21, 1992, abandoned.

[51] Int. Cl.[7] ..................................................... A61B 17/04
[52] U.S. Cl. .......................... 606/151; 606/213; 604/159; 604/164
[58] Field of Search .................................. 606/213, 151, 606/215, 158, 108

[56] References Cited

U.S. PATENT DOCUMENTS

| | | |
|---|---|---|
| 3,124,136 | 3/1964 | Usher . |
| 3,874,388 | 4/1975 | King et al. . |
| 4,007,743 | 2/1977 | Blake . |
| 4,031,569 | 6/1977 | Jacob . |
| 4,665,906 | 5/1987 | Jervis . |
| 4,917,089 | 4/1990 | Sideris . |
| 4,994,077 | 2/1991 | Dobben . |
| 5,067,957 | 11/1991 | Jervis . |
| 5,108,420 | 4/1992 | Marks . |
| 5,171,259 | 12/1992 | Inoue . |
| 5,190,546 | 3/1993 | Jervis . |
| 5,258,000 | 11/1993 | Gianturco . |
| 5,334,217 | 8/1994 | Das . |
| 5,578,045 | 11/1996 | Das . |
| 5,597,378 | 1/1997 | Jervis . |
| 5,643,317 | 7/1997 | Pavenik et al. . |

FOREIGN PATENT DOCUMENTS

| | | |
|---|---|---|
| 0 547 530 | 6/1993 | European Pat. Off. . |
| 2 641 692 | 7/1990 | France . |
| 28 22 603 | 11/1979 | Germany . |
| 233 303 | 2/1986 | Germany . |
| 1468511 | 3/1989 | U.S.S.R. . |
| WO 90/09763 | 9/1990 | WIPO . |
| WO 90/14796 | 12/1990 | WIPO . |
| WO 93/13712 | 7/1993 | WIPO . |

OTHER PUBLICATIONS

Rome et al. "Double'Umbrella Closure of Atrial Defects—Initial Clinical Applications", Circulation, 82:751–758 (1990).

King et al., "Nonoperative Closure of Artial Septal Defects", Surgery [75] No. 3, pp. 383–388 (Mar. 1974).

Rocchini, "Editorial Comment—Transcatheter Closure of Atrial Septal Defects: Past, Present and Fugure", Circulation, 82:1044–1045 (1990).

*Primary Examiner*—Gary Jackson
*Attorney, Agent, or Firm*—Fredrikson & Byron, PA

[57] ABSTRACT

The present invention provides a system and a method for closing septal defects and the like. The system includes a closure device having a pair of occluding disks, each disk being formed of a membrane and an elastically deformable frame carried about the periphery of the membrane. The frame, which may be formed of a superelastic material, is capable of being collapsed for passage through a catheter and elastically returning to a predetermined shape for tautly holding the membrane. A central portion of the membrane of each disk is attached to a central portion of the other membrane to define a conjoint disk. The method of the invention involves collapsing the frames of the disks, inserting the closure device into a catheter, and positioning the distal end of the catheter adjacent a septal defect. The first disk is then urged out of the distal end of the catheter to permit its frame to elastically return to a predetermined shape, pulling the membrane taut on one side of the defect. The second disk is then similarly deployed on another side of the defect, automatically positioning the conjoint disk within the defect to occlude it.

6 Claims, 9 Drawing Sheets

SEPTAL DEFECT CLOSURE DEVICE

The present application is a divisional application of U.S. patent application Ser. No. 08/756,776, filed Nov. 26, 1996, now pending, the teachings of which are incorporated herein by reference; which is a divisional application of U.S. patent application Ser. No. 08/284,766, filed Aug. 2, 1994, now U.S. Pat. No. 5,578,045; which is a divisional application of U.S. patent application Ser. No. 08/062,095, filed May 14, 1993, now U.S. Pat. No. 5,334,217; which is a divisional application of U.S. patent application Ser. No. 07/822,951, filed Jan. 21, 1992, now abandoned.

BACKGROUND OF THE INVENTION

The present invention generally relates to devices and methods for occluding septal defects or shunts in the heart or the vascular system. In particular, the present invention provides a device for closing such defects which may be delivered through a catheter and a method for delivering and deploying that device to close off the defect.

A septum is generally defined as a thin wall of muscle or other tissue which divides two or more chambers or other areas within the body. The term "septal defect" generally refers to a perforation or other hole which passes through a septum. Ventricular septal defects, atrial septal defects and patent ductus arteriosus are the three most common congenital cardiac malformations. Of these three malformations, atrial septal defects are the easiest to approach through a transcatheter approach and the defects themselves are located away from the atrioventricular valve apparatus. These defects have been surgically corrected for decades.

Initially, atrial septal defects were corrected by open heart surgery. In such an operation, the surgeon would have to open the chest of a patient and bypass the heart temporarily, e.g., by means of a mechanical heart or a "heart-lung machine." The surgeon would then physically cut into the heart and suture small defects closed. In the case of larger defects, a patch of a biologically compatible material would be sewn onto the septum to cover the defect. An atrial septal defect makes the heart muscles work considerably harder because of shunting of blood through the defect and, if left untreated, leads to high pulmonary arterial pressures, and this additional strain placed on the heart muscles can cause fatal heart failure.

In order to avoid the morbidity and mortality associated with open heart surgery, a variety of transcatheter closure techniques have been attempted. In such techniques, an occluding device is delivered through a catheter. Once the closure device is positioned adjacent the defect, it must be attached to the rest of the septum in a manner which permits it to effectively block the passage of blood through the defect.

The first such closure device was proposed by King and Mills nearly 20 years ago and is described in U.S. Pat. No. 3,874,388 (1975), the teachings of which are incorporated herein by reference. The King closure device comprises a pair of complex mechanical umbrellas, with each umbrella having a plurality of arms extending radially from a central hub. The hubs of the two umbrellas are mechanically connected to one another and each umbrella includes a fabric covering over the arms, much like a common umbrella. The ends of each arm are provided with barbs which are anchored into the septum to hold the occluder in place. Although this device represents a significant improvement over open heart surgery, the complex mechanical umbrellas prove rather difficult to unfold after passage through a catheter, requiring an array of cables to deploy the arms. This makes proper placement of the device difficult, and the barbs on the arms prevent retraction or repositioning of the device once it is in place. Use of this device has been limited to adult patients because the device requires a large catheter, such as about 23 French (7.3 mm), for delivery.

Rashkind proposed a single-umbrella closure device which was capable of delivery through a 5 mm system, which permitted use in children weighing at least about 20 kg. Similar to the King device, this umbrella utilizes barbed hooks on the ends of umbrella arms to ensure attachment to the septum, and the single umbrella is placed on the left side of the atrial septal defect. The barbs once again prevented disengagement of the device, and poorly centered devices were common. This device had limited acceptance in the field due to the positioning difficulties because malpositioned or improperly seated devices frequently required open heart surgery for correction.

Due to the low success rate of these devices, Lock and others developed a "modified double-umbrella Rashkind occluder" in which the arms of the device are hinged to permit them to fold back against themselves. Lock's "clamshell" occluder did not include barbs at the end of the radial arms of the umbrella, allowing its position to be readjusted or retrieved. Furthermore, the structure of this umbrella was somewhat more compact than the earlier King or Rashkind umbrellas, allowing deliver through an 11 French (3.7 mm) catheter, enabling the device to be used to treat children weighing 8 kg or more.

More recently, Sideris has proposed an occlusion device which combines a single umbrella with a separate anchoring device. This occluder is shown in U.S. Pat. No. 4,917,089. Like the previous defect occlusion devices, Sideris' invention utilizes an umbrella with a plurality of radially extending arms. A string connects the arms of this umbrella to a generally rhomboidally shaped anchor which includes an internal wire skeleton and a central, rhomboidally shaped piece of rubber. The string attached to the struts of the umbrella is affixed to the central rubber element of the anchor. The anchor is placed on the opposite side of the septum from the umbrella and the length of the string limits movement of the occlusion device with respect to the septum.

All of the prior art devices described above share two defects in common. Firstly, all of these systems are rather mechanically complex and require a great deal of remote manipulation for deployment, such as by applying tension to one or more cables in order to deploy the arms of an umbrella or to anchor the device in place. This extensive remote manipulation not only increases the difficulty of the procedure, but tends to increase the likelihood that the device will be improperly deployed and require either retrieval or repositioning.

Secondly, all of these devices are essentially two separate members which are joined to each other at a single point or pivot. When the left atrial member is opened, the central point would tend to ride to the lower margin of the defect; proper centering of the device is quite difficult. The Lock device does form a 'cone' when traction is applied to help centering. In order for this to effectively occur, though, the device has to be pulled perpendicular to the plane of the atrial septum. In a beating human heart, this is rather difficult to achieve.

It would therefore be desirable to provide a simple, compact closure device which may be delivered through a small catheter to permit the treatment of younger children. It would also be highly advantageous to have such an anchoring device which can be readily deployed with a minimum of remote manipulation. In addition, a device which is truly self centering and self occluding would be superior to these prior art devices.

SUMMARY OF THE INVENTION

The present invention provides a simple, reliable device for effectively occluding a septal defect. The instant closure device includes first and second occluding disks which are attached to one another. Each disk comprises a membrane having an elastically deformable frame carried about its periphery. The frame is capable of being collapsed so that the device may be delivered through a catheter, but should be flexible enough to permit it to elastically return to its initial shape upon exiting the catheter to pull the membrane taut. A central portion of the membrane of each disk is affixed to a corresponding portion of the membrane of the other disk, thereby attaching the two disks directly to one another at their centers. The affixed central portions of the two membranes defines a central "conjoint disk" of the device, and this conjoint disk is sized to be received within a septal defect.

The present invention also contemplates a method of delivering this septal defect closure device. The frames of the two disks are collapsed and the device is inserted into the distal end of a delivery catheter. This is passed coaxially through an outer guiding catheter which is positioned within a patient's vascular system across the septal defect being treated, and the first of the two disks is urged out of the catheter on one side of the defect. The flexible frame of the disk elastically returns to its initial shape, expanding the disk and pulling the membrane taut. The second disk may then be urged out of the distal end of the catheter on the other side of the defect. The frame of this second disk pulls the attached membrane taut, leaving the central conjoint disk of the device within the defect.

A septal defect closure device of the invention is simple in construction, greatly enhancing the mechanical durability of the device and therefore reducing the risks associated with its use. Additionally, because the closure device relies upon elastically deformable frames which automatically assume their initial shape upon exiting a catheter, it can be deployed to occlude a defect without complex remote manipulation by the operator.

DESCRIPTION OF THE PREFERRED EMBODIMENTS

Figure 1:
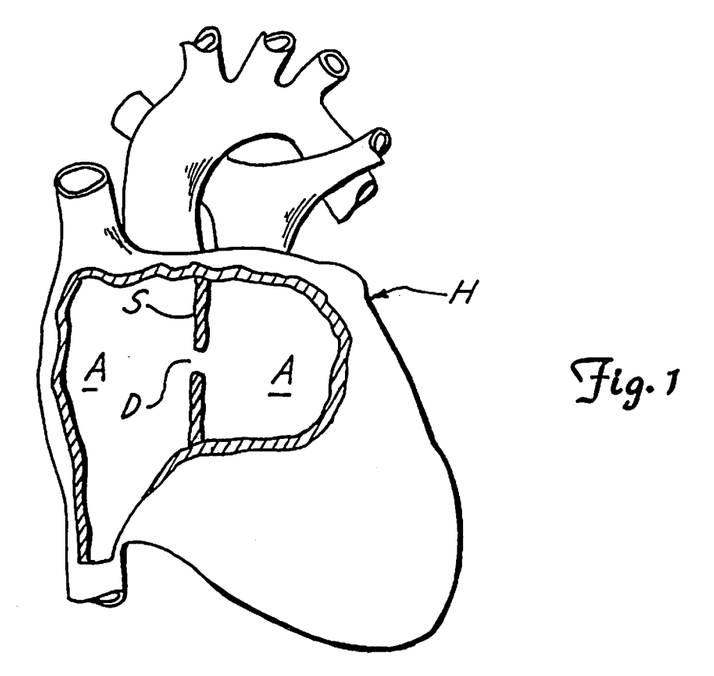
FIG. 1 is a partially broken-away view of a heart having an atrial septal defect.

FIG. 1 represents a heart H having a septum S dividing the two atria A,A. A defect D is shown as a port extending through the atrial septum. A normal atrial septum serves to effectively divide the two chambers A,A and separate the blood passing through the heart. As shown in FIG. 1, though, the septal defect prevents the septum from fulfilling its function in that it permits blood to pass from one chamber to the other as the heart pumps. The presence of a significantly large atrial septal defect causes blood to shunt across the defect from the left atrium to the right atrium and hence on to the right ventricle and pulmonary arteries to the lungs. This increases the blood flow to the lung. If the defect is not closed, over a period of time this leads to an increase in the pressure in the pulmonary arteries and right side of the heart, and shunting of unoxygenated blood from the right to the left side, leading to death due to cardiac failure, hemoptysis or cerebral stroke due to blood clots passing from the veins through the atrial defect into the cerebral circulation. In patients with significant sized ventrical septal defects or patent ductus arteriosus, there is shunting of blood from the high pressure left ventricle or aorta, into the right sided chambers and pulmonary arteries which normally have much lower pressures. The torrential increase in flow at a high pressure can lead to cardiac failure and death, apart from the serious long-term complication of high pulmonary pressures causing a reversal of the direction of the shunt.

Figure 2:
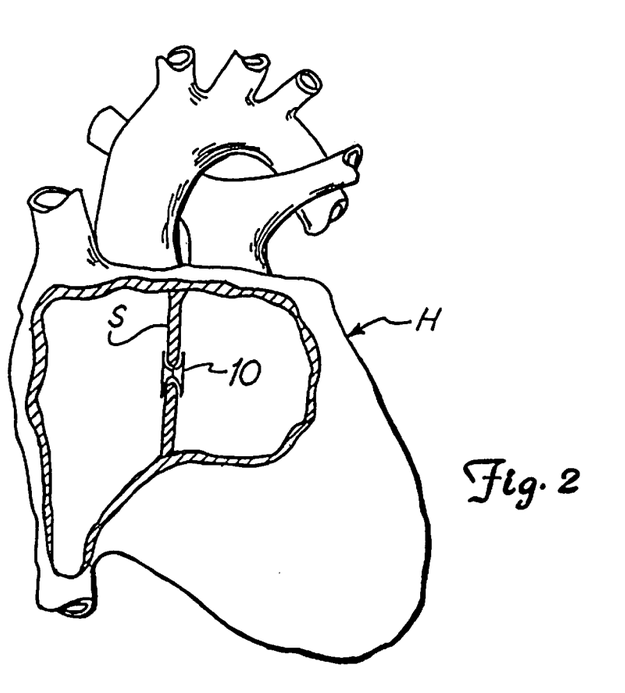
FIG. 2 is the heart of FIG. 1 showing a septal closure device of the invention occluding the atrial septal defect.

As shown generally in FIG. 2, a septal defect closure device 10 of the invention may be attached to the septum to effectively block the defect. As described in detail below, once the closure device is in place it will become anchored to the septum and prevent the flow of blood through the septum to the adjoining chambers of the heart. This will permit the heart to operate normally.

Figure 3:
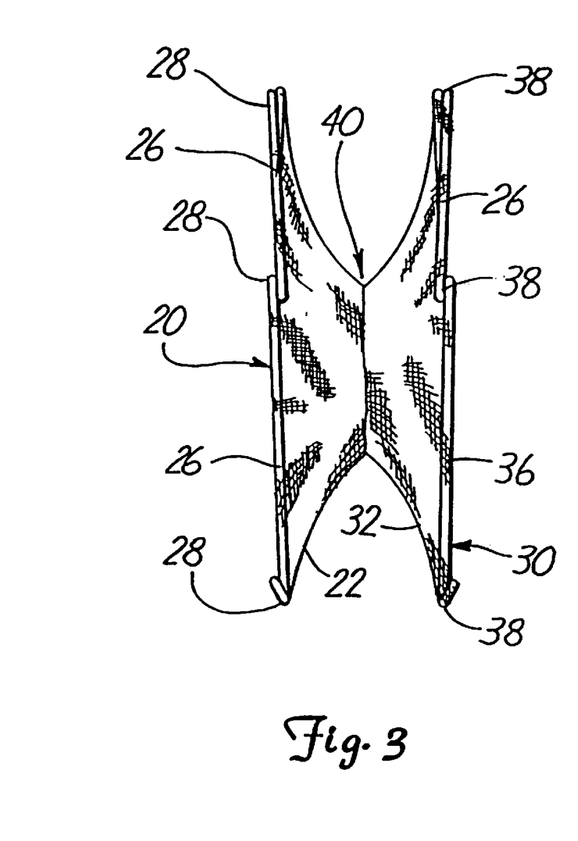
FIG. 3 is a partially expanded side view of a preferred embodiment of a septal closure device of the invention.
Figure 4:
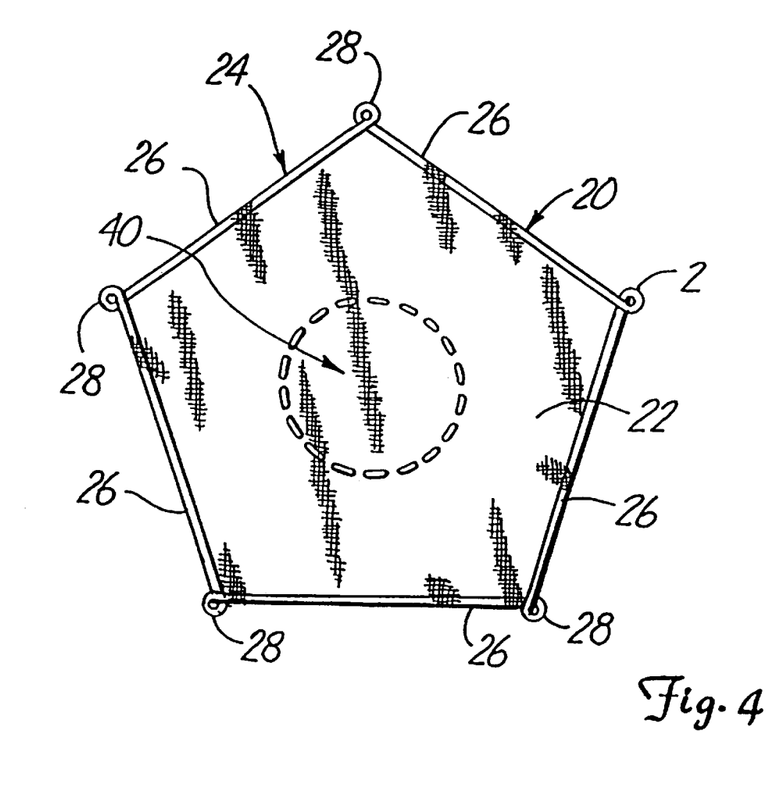
FIG. 4 is a front view of the closure device of FIG. 3.

One preferred embodiment of the invention is shown in FIGS. 3 and 4. As best seen in FIG. 3, the closure device includes two disks 20,30. Each disk generally comprises a membrane 22,32 which may be of any desired shape. In the embodiment shown in FIGS. 3–8, the membrane is preferably formed of a thin, flexible material, such as a fabric which may be folded and pulled taut without being damaged. Elastic polymeric materials such as nylon, polyester, polypropylene, polytetrafluoroethylene (Teflon), and expanded polytetrafluoroethylene (GoreTex), as well as natural fabrics such as silk, have been found to work quite well, with elastic nylon appearing to be the best material for the present purposes. Alternatively, the membrane may be formed of a thin piece of a superelastic material, such as a thin sheet of NiTi alloy or a superelastic polymeric composite.

A frame 24,34 is attached to and desirably extends substantially around the periphery of the membrane. When the frame is in its natural, non-deformed state, as shown in FIGS. 3 and 4, it serves to hold the membrane 22,32 taut. In FIG. 3, the frames of the two disks 20,30 are shown as being spaced from one another for purposes of the present explanation, but this is not the normal configuration of the disks. Normally, the frames 24,34 of the device pull their respective membranes 22,32 into a taut, generally planar shape, and the two frames will generally abut against one another.

The membranes 22,32 may be attached to their respective frames 24,34 by any suitable means. For instance, the membrane may be directly attached to the frame by means of an adhesive or the like. Preferably, though, the periphery of the membrane is wrapped about the frame and the peripheral edge (not shown) is attached to the rest of the membrane, essentially defining a sleeve about the frame. The sleeve may fit the frame relatively loosely so that the frame may move within the sleeve with respect to the membrane. The peripheral edge of the membrane may be affixed to the rest of the membrane in any suitable fashion, such as by sewing in the case of a fabric membrane. If a thermosetting polymeric material, e.g., nylon, is used, the peripheral edge may be fused to the rest of the membrane by means of heat sealing or the like. Alternatively, if the membranes are themselves formed of a superelastic material, they will tend to return to their original shape without a frame, so the frame may be omitted if so desired.

The frame desirably comprises a plurality of elongate legs 26, with each leg being flexibly connected to another leg at each end. Any suitable number of legs may be employed, and the legs may be shaped as desired. For instance, in FIGS. 3 and 4, the frame has five substantially straight legs and is therefore generally pentagonal in shape. FIGS. 5A–F illustrate a number of alternative embodiments of frames of the invention which utilize a variety of different numbers and shapes of legs. The reference numerals used in FIG. 5 correspond to those used in FIGS. 3 and 4 with respect to the first frame 20, but bear an additional alpha suffix ranging from A to F.

Figure 5A:
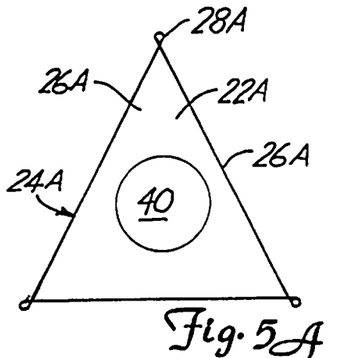
FIG. 5A–F depict alternative embodiments of a closure device of the invention.
Figure 5B:
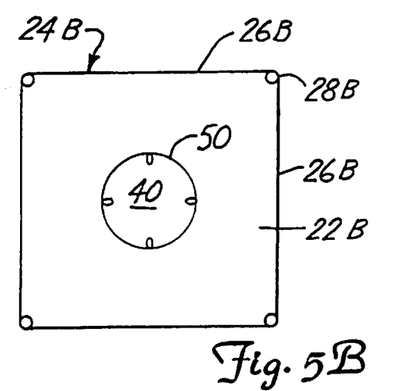
Figure 5C:
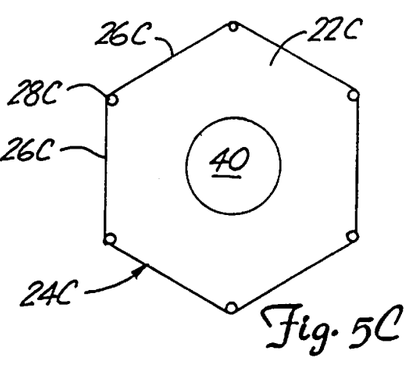
Figure 5D:
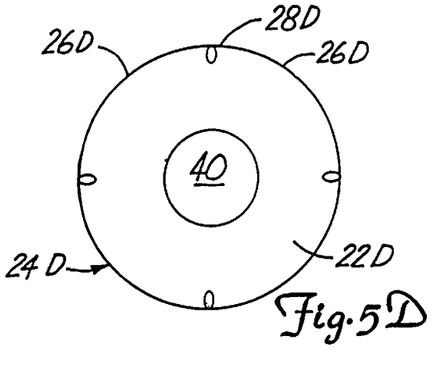
Figure 5E:
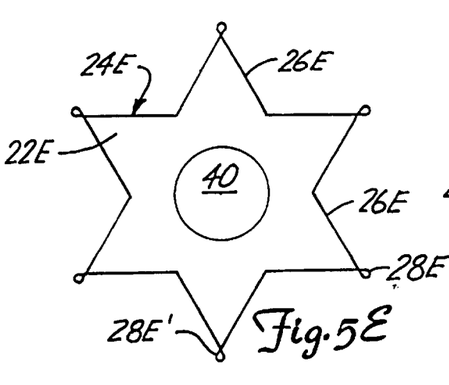
Figure 5F:
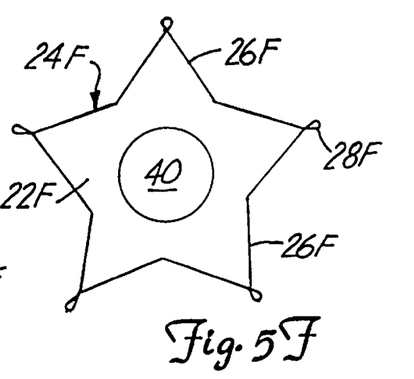

In FIGS. 5A–C, the legs are all generally straight and range in number from three to six. Obviously, if the legs are straight, at least three legs must be provided to adequately extend about the periphery of the membrane. In FIGS. 5D–F, the legs are not straight, but rather are more complex in shape. Legs 26D (FIG. 5D) are generally arcuate in shape, with four legs defining a generally circular frame 24D. Although one such curved leg could extend about the entire periphery of the membrane 22D to provide a frame 24D consisting of a single leg, for reasons set forth below it is preferred that the frame include at least two interconnected legs. In FIGS. 5E and F, each leg is bent at an obtuse angle at approximately the middle of its length. When inserting the frame into a catheter as detailed below, these bends in the legs permit the frame to be collapsed more readily. The angle of the bends in the legs may be adjusted as desired to achieve the desired frame configuration. Although the frames shown in FIG. 5 all have legs which are substantially equal in length, the legs of any given frame may vary in length if so desired.

The legs of a frame may be connected to each other in any useful fashion. FIGS. 3 and 4, however, show a preferred way of connecting the legs. As noted above, the legs 26,36 of a frame 20,30 are flexibly connected to another leg at each end. A resilient loop 28,38 is disposed between adjacent ends of two legs and one end of the loop is attached to each leg. These loops desirably lie generally in the same plane as the legs and may extend generally outwardly of the periphery of the disk (as shown in FIGS. 3, 4, 5A, and 5E–F), or may extend generally inwardly of the periphery of the disk (as shown in FIGS. 5B–D). As shown in FIG. 5, each of the loops may be of substantially the same size, for instance in the range of about 1 mm to about 3 mm in length. Alternatively, as shown in FIG. 5E, the frame may be provided with a plurality of relatively small loops 28E and a plurality of relatively long loops 28E', which may desirably range from about 5 to about 15 mm in length. These longer loops 28E' are desirably spaced about the periphery of the closure device and extend generally radially outwardly of the periphery of the disk. When the disk is deployed to block a septal defect or the like, these longer loops can serve as bracing struts which will effectively engage the tissue surrounding the defect being closed without requiring any significant increase in the size of the disks employed or the catheter used to deliver to device.

The loops 28,38 are desirably formed to function as tension springs, biasing the legs to which they are attached outwardly into the position shown in FIGS. 3 and 4. This will help ensure that the frame will elastically return substantially to its initial configuration even after it has been collapsed and delivered through a catheter, as set forth below.

Figure 6:
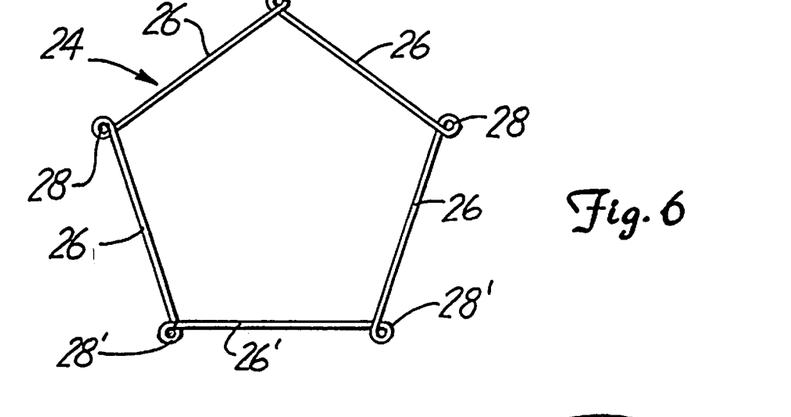
FIG. 6 is a front view of a frame for use in the closure device of FIG. 3.
Figure 7:
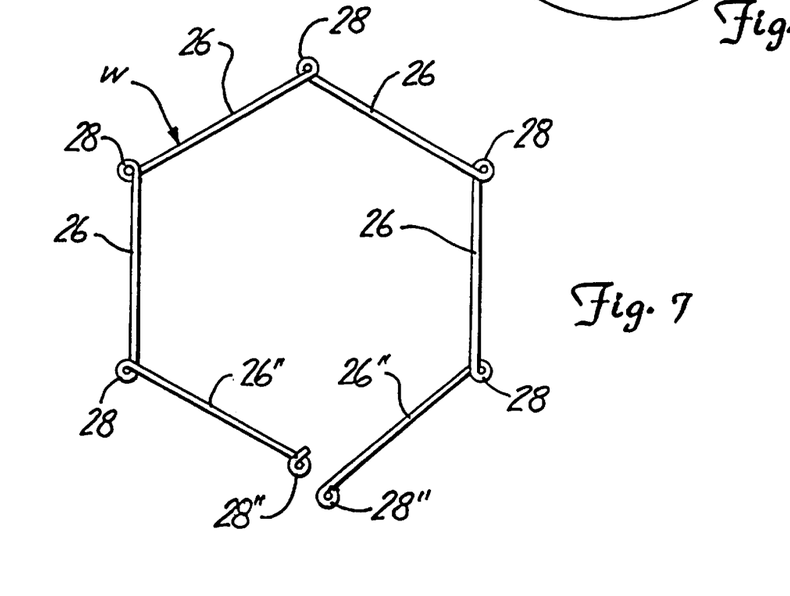
FIG. 7 is a front view of the frame of FIG. 6 in its unassembled form.

In a particularly preferred embodiment, each frame 20,30 is formed integrally of a single elongate strand of wire W. As best seen in FIGS. 6–7, each of the legs 26 may simply comprise a length of the wire and the wire may be twisted between adjacent legs to define the loops 28. The ends of the wire may be attached to each other in any secure fashion, such as by means of a weldment or a suitable biocompatible cementitious material.

In the embodiment shown, however, one leg 26' comprises two overlapping lengths of wire. Then the wire W is formed into the shape of the frame, one more leg-like length than is otherwise necessary is formed. The two end lengths 26" of the wire are then laid over and affixed to one another, yielding a frame having the desired number of legs. Desirably, both of the end lengths 26" are approximately the same length and end loops 28" are provided at the ends of the wire. As shown in detail in FIG. 6A, these end loops 28" may be interlocked with the loop 28 between the opposite end length 26" and its adjacent leg 26. By so interlocking these loops to form an overlapping loop 28' at each end of the overlapped leg 26', the two end lengths 26" of the wire may be effectively joined to one another to define the overlapped leg.

Figure 6A:
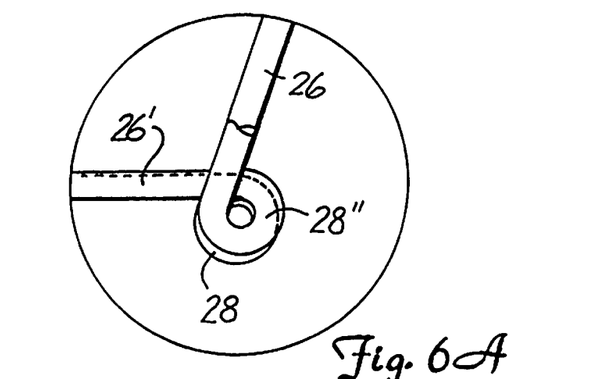
FIG. 6A is an enlarged isolation view of the encircled portion of FIG. 6.

If so desired, the end lengths 26" may be further secured to one another by means of a weldment or a suitable adhesive, as noted above, or a suture (not shown) may be tied about each overlapping loop 28' to hold that loop together. In order to provide further security, rather than simply using two short, separate sutures to secure the two end loops, a single, longer suture may be used. The suture may be tied at one end to one loop and at its other end to the other loop, with an intermediate length of the suture being helically wound about the overlapping leg 26' to ensure that the two end lengths 26" are firmly attached to one another.

The frame 20 should be formed of a flexible, elastically deformable material, such as a metal. In a particularly preferred embodiment, the wire comprising the frame is formed of a superelastic material. One such material currently known in the art is a near-stoichiometric nickel/titanium alloy, commonly referred to as Nitinol or NiTi. Such superelastic (also referred to as "pseudoelastic") materials may be elastically deformed to a much greater extent than most other materials yet substantially fully recover their original shape when released. This permits the frame 20 to be deformed sufficiently for insertion into and passage through a small-diameter catheter yet automatically elastically return to its initial shape upon exiting the catheter. In an alternative embodiment, the preferred shape of the frame may be cut out from a sheet of such superelastic material as a single block, by chemical etching, punching with a suitable punch and die, or any other appropriate forming method.

In order to enhance radiopacity so that the frame can be viewed remotely during deployment, the frame may be provided with a radiopaque coating, such as gold or platinum. For instance, the wire W may be plated with a thin layer of gold or platinum. In one particularly useful embodiment, a helically wound length of a thin radiopaque wire (not shown) is placed over the wire W; such core/coil structures are well known in the art and need not be discussed at length here. In order to ensure that the frame can be collapsed into the smallest possible configuration for delivery through small catheters, the diameter of the wire comprising the frame should be kept small. For instance, the wire W may be about 9 mils (0.009") in diameter and the radiopaque outer wire may be about 1–3 mils (0.001–0.003") thick, for a total outer diameter of about 11–15 mils (0.011–0.015"). Although the outer wire may extend along the entire length of the frame, it is preferred that it be provided only along the legs 26, leaving the loops 28 as short lengths of the bare wire W.

Alternatively, radiopaque marking bands (not shown), which are commercially available, may be employed. By placing one such band on each leg 26 of the frame, the surgeon can remotely visualize the frame as a plurality of small bands; when the bands are appropriately spaced from one another on a monitor, the surgeon will know that the frame is properly deployed.

Referring back to FIGS. 3 and 4, a septal defect closure device of the invention includes a central conjoint disk 40. A central portion of each membrane 22,32 is attached to a corresponding central portion of the membrane of the other disk. The central conjoint disk 40 may be of any desired shape, but the generally circular shape shown in FIGS. 3–5 is preferred.

The membranes 22,32 may be affixed to one another by any desired means, such as a biocompatible adhesive. The adhesion between the two central membrane portions should be strong enough to ensure that the two disks will not become separated from one another during handling and deployment of the closure device. In one preferred embodiment, the membranes are sewn to one another, with the stitching defining the shape and size of the conjoin disk 40. If the membranes are formed of an appropriate polymeric material their central portions may instead be fused to one another by means of heat sealing or the like. As another alternative embodiment, the membranes 22,32 may be formed of a thin, highly flexible material such as a nylon and the conjoin disk may include another piece of material (not shown), such as polyurethane, nylon, a superelastic material such as nitinol, or the like. This additional material is desirably disposed between the two membranes and sewn or otherwise bonded to the membranes in defining the conjoint disk. The additional material may be of any size, but is desirably approximately the same size as the conjoint disk, or slightly larger.

If so desired, the central conjoint disk may include an internal frame 50 as shown in FIG. 5B. This internal frame is desirably constructed in substantially the same manner as the frames 20,30 described above. However, the internal frame 50 is desirably smaller in size than the frames 20,30 and is sized to be attached directly to the peripheral edge of the conjoint disk 40. The internal frame 50 is desirably bonded to and generally positioned within the conjoint disk such that when the device is deployed, this small, internal frame will assist in the immediate, taut deployment of the conjoint disk within the defect.

In order to facilitate relatively quick closure, the conjoint disk is desirably sized to substantially fill the defect being occluded, but should not be substantially larger than the defect. Although the size of septal defects tend to vary, most atrial septal defects are smaller than 25 mm in diameter. Accordingly, it is contemplated that a variety of closure devices having central conjoint disks ranging in size from about 5 to about 30 mm will be provided. A surgeon may measure the size of the defect by known means, e.g., using a balloon catheter filled with a contrast medium, and select a closure device having a 'conjoint disk' of the appropriate size.

For reasons set forth more fully below, it is also desirable that the disks 20,30 be at least 1.6 times the size of the defect, and preferably range from about 1.6 to about 2.5 times the size of the defect. The difference between the stretched diameter of the septal defect, as determined by measurement with a balloon catheter or by other known means, and the size of the frame is optimally approximately 15 mm. Since the central conjoint disk 40 is chosen to approximate the size of the defect, the maximum dimension of the frame may be at least 1.6–2.5 times the size of the conjoint disk. As an example, to patch a 10 mm defect, a closure device having a central conjoint disk about 10 mm in diameter and a frame of about 25 mm in maximum dimension may be selected.

Figure 12:
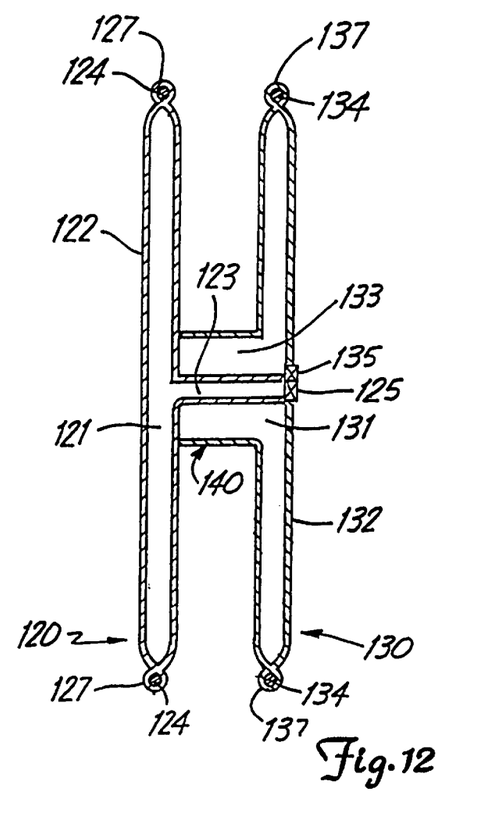
FIG. 12 is a cross-sectional view of an alternative embodiment of a septal closure device of the invention.

An alternative embodiment of the present invention is shown in cross-section in FIG. 12, wherein like numbers have been used, but differ from the numbers in FIGS. 3–10 by 100. As shown in FIG. 12, the first disk 120 comprises a membrane 122 supported by a frame 124. However, unlike the embodiment described above, the membrane 122 of the present invention is not a single layer of fabric, but is rather a flexible, collapsible balloon-type member which can be inflated to define an internal cavity 121. Similarly, the second disk 130 is supported by a frame 134 and the membrane 132 may be inflated to define an internal cavity 131. The membranes 122,132 may be formed of any suitable material, such as a thin, flexible latex or the like. Inflatable, detachable balloon-type structures are known in the art and may be delivered by known transcatheter techniques. The membranes 122,132 may be attached to the frames 124,134 by any suitable means, such as by a weldment 127 internally formed with the membranes which substantially encases the frame 124, as shown.

The conjoint disk 40 of the embodiment described above simply comprises central portions of each of the membranes 122,132 which are bonded to one another, as described above. In the embodiment shown in FIG. 12, though, the conjoint disk 140 is somewhat more complex in structure. The membrane 122 of the first disk 120 includes an inflation port 123 which is operatively connected to a check valve 125. In the preferred embodiment shown, the check valve 125 is disposed on the second disk 130 at a location disposed away from the first disk 120. This check valve 125 is desirably disposed immediately adjacent a similar check valve 135 associated with the second disk 130. These check valves may in turn be connected to a detachable, dual lumen inflation catheter (not shown) as is known in the art for such techniques as balloon embolization and the like. This catheter permits an operator to selectively deliver a fluid through a check valve to inflate the associated disk. The inflation catheter should be detachable from the check valves after the device is deployed.

In the embodiment shown wherein the check valve is disposed away from the first disk 120, the inflation port 123 desirably extends through the conjoint disk 140 and may be centrally located therein. The rest of the conjoint disk may be defined by a short, generally tubular segment 133 of the second disk and the inflation port 123 of the first disk may extend through this tubular section. The diameter of the conjoint disk is desirably sized to substantially fill the defect being blocked, as described above in connection with the previous embodiment.

FIG. 12 depicts the present embodiment once it has already been inflated. In deploying the closure device 110, though, the membranes 122,132 preferably are not inflated, but are desirably substantially empty so that they will remain flexible. Thus, the structure of this deflated closure device substantially corresponds to the overall structure of the previous embodiment and may be delivered to the defect and deployed in a similar manner. However, once the first disk 120 is opened on the distal side of the defect by the action of the frame, it may then be inflated. This may be accomplished by delivering a suitable fluid through the check valve 125 and inflation port 123 to inflate the membrane 122. The fluid will then expand the membrane to define and fill the cavity 121. Although any suitable fluid may be used, it is preferred that a biologically compatible, self-curing cementitious material, such as an epoxy or a cyanoacrylate, be used. In this manner, the cavity 121 may be filled with this material and permitted to substantially harden, creating a stable, generally rigid structural member from the membrane 122.

As in the previous embodiment, the closure device may then be retracted until the first disk 120 engages the septum and the second disk 130 may then be deployed. The frame 134 will then tend to cause the membrane 132 to engage the septum as in the previous embodiment. Although this would serve to effectively close the defect, the second membrane may also be inflated in a like manner to fill the cavity 131 with a suitable fluid, such as that described above. This will serve to provide relatively rigid structural support, as with the first disk 120, but it will also serve to inflate the tubular segment 133 of the conjoint disk 140, more effectively closing the defect by expanding the disk 140.

Figure 10:
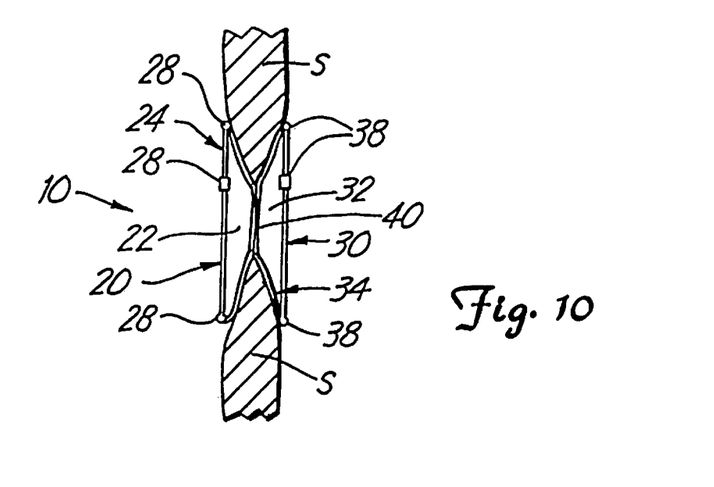
FIG. 10 schematically depicts the closure device of FIGS. 8 and 9 with the second disk expended on the other side of the septal defect.

FIG. 10 depicts a closure device 10 of the invention deployed to occlude a defect in a septum S. The first disk 20 of the device is positioned on one side of the defect while the second disk 30 is generally disposed on the other side. The frames 24,34 of the disks are elastically biased toward the position shown in FIG. 4, pulling their respective membranes 22,32 taut. The central conjoint disk 40 is positioned within and substantially closes off the defect. As explained above, the taut membranes are generally planar and the frames 24,34 generally abut against one another when the device is unconstrained. Because the frames are elastically biased toward their constrained configuration, they are biased generally toward one another and engage opposing sides of the septum about the defect. Since there are no compressive forces acting on the frames which might cause them to collapse, this serves to effectively hold the device in place with the conjoint disk 40 positioned within the defect, as shown.

The membranes are formed of a relatively porous material. At first glance this may seem to contradict the purpose of the device, i.e., to block the flow of blood across the device, and hence the septum. However, blood will tend to coagulate in the conjoint disk after it has been in place for some time; blood flow across the conjoint disk is usually substantially blocked after about 10–20 minutes. If so desired, the conjoint disk (or the entire device) may be treated with a thrombogenic agent to speed this natural process or may be impregnated with a biocompatible polymeric compound or the like to make it relatively impervious to fluids.

The primary purpose of using a porous material for the membranes is to accelerate the process of permanently anchoring the device in place. The frames 24,34 hold the membranes tautly and in intimate contact with the outer surface of the septum S, as shown in FIG. 10. This intimate contact between the septum and the porous membranes permits ingrowth of collagen and fibrous tissue from the septum into the membranes. Over time, the membrane resting against the septum will become securely anchored to the septal wall and be covered by a layer of endothelial cells.

The design of this device is in stark contrast to the septal defect closure devices known in the art. As explained in some detail above, all of the prior art devices employ a mechanical umbrella of one design or another. The radially extending arms of the umbrella contact the septum and serve to space all but the peripheral edge of the umbrella away from the septum. Endothelial cells, collagen and fibrous tissue are therefore permitted to grow into only the very periphery of the umbrella. Thus, while a closure device of the invention essentially becomes an integral part of the septum, the complex mechanical structure of prior art devices does not yield as complete integration as the present invention.

The mechanical complexity of prior art devices also tends to markedly affect their durability. In the case of atrial or ventricular septal defects, for example, the heart obviously continues to beat after the device is in place. Since beating of the heart is accomplished by flexure of the heart muscles, the septum will flex to some degree with every beat of the heart. The radial arms must therefore flex with the septum each and every time the heart beats. The number of cycles of this stress-inducing movement produces repeated stresses on the arms, which can eventually lead to mechanical failure and fracture of the arms.

When a closure device of the invention is deployed, the centrifugal tension of the outer frame opens the disk to occlude the defect. Since there are no radial arms to prop open the device, the occurrence of repeated flexion does not occur due to the beating of the heart or pressure differences between the cardiac chamber during the phase of contraction of the heart. To the contrary, any pressure difference would drive the frame and disk against the septum, more firmly occluding the defect, in much the same manner as a bathtub stopper. In addition, the superelastic material of the frame tolerates flexural stresses much better than the rigid steel arms of the prior art devices. The present device therefore will continue to flex with the septum without any significant effect on its structural integrity.

As stated above, the present invention also contemplates a method of delivering and deploying the closure device 10 described above. According to this method, the device is delivered to the site of the septum by a transcatheter procedure, eliminating the need for open heart surgery and all of its attendant risks.

The device is inserted into the distal end of a catheter C by collapsing the frames of the disks. The frame 24 of the first disk 20 is collapsed and inserted into the end of the catheter first. This may be accomplished in any suitable manner, such as by manually folding the frame and placing it into the catheter. In a preferred embodiment, however, the loops 28 are used as eyelets to assist in collapsing the frame. A thread, such as a length of a suture thread, is passed through all of the loops of the frame and is drawn tight. Similar to a conventional purse string. This will cause the ends of the legs 26 to generally converge upon a single point spaced axially outwardly of the central conjoint disk 40. These converging ends may be inserted into the distal end of the catheter, and the thread passing through the loops may be removed by simply pulling on one of its ends. The rest of the first disk 20 can then be urged into the catheter and the walls of the catheter will further collapse the frame 24 upon itself, folding each of the legs. As noted above in connection with FIGS. 5E and F, if the legs are already bent, this insertion will tend to be easier.

Figure 8:
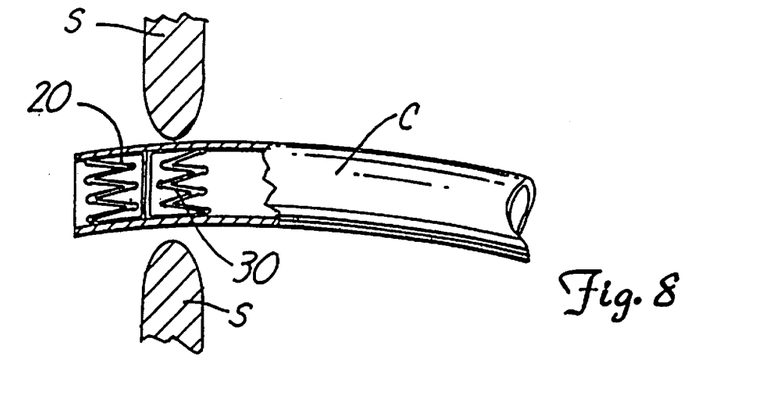
FIG. 8 schematically depicts a closure device of the invention collapsed inside a catheter for delivery to a septal defect.

The second disk 30 may be folded in the same manner if so desired. This can also be accomplished by simply continuing to urge the device into the catheter, though. The walls of the catheter will act against the legs 36, generally folding them such that their ends will generally converge on a point spaced axially outwardly of the central conjoint disk 40, much like the first frame 24. Obviously, the ends of the legs 26 of the first disk will converge on a point spaced distally of the conjoint disk while the ends of the legs 36 of the second conjoint disk will converge on a point spaced proximally of the conjoint disk. The device will therefore be configured within the catheter generally as schematically shown in FIG. 8, though the ends of the legs will tend to be closer to one another than is depicted in that drawing.

Either before or, preferably, after insertion of the closure device into the catheter C, the distal tip of the catheter is positioned adjacent the septal defect D to be occluded. A distal portion of the catheter should extend through the defect to position the distal tip of the catheter on the distal side of the defect, as shown in FIG. 8. The closure device is urged through substantially the entire length of the catheter such that it is positioned near the distal tip of the catheter, also as shown in FIG. 8. Once again this may be done either before or after positioning of the catheter, but it is desirably done before so that the distal tip of the catheter will not be inadvertently moved out of position as the device is advanced.

Figure 9:
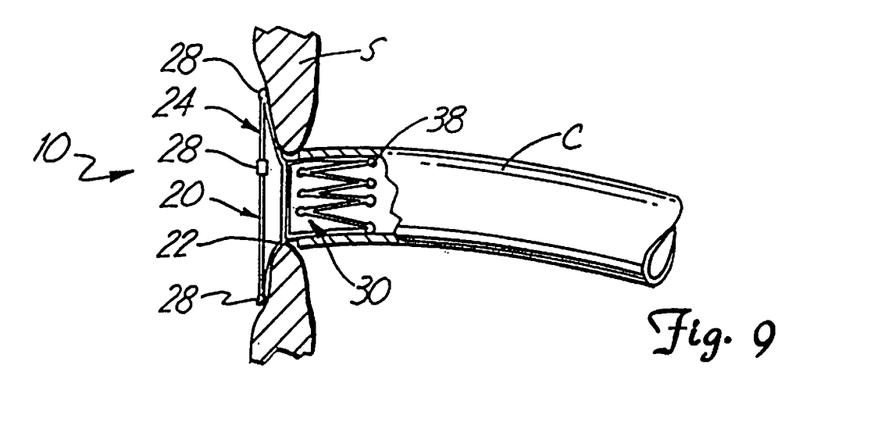
FIG. 9 schematically depicts the closure device of FIG. 8 with the first disk expanded on one side of the septal defect.

Once the catheter is properly positioned, the first disk 20 of the device is urged out of the distal end of the catheter. With the constraint of the catheter walls removed, the frame 24 will elastically substantially return to its initial, non-deformed shape (FIG. 4) and pull the membrane 22 taut. The catheter C may then be retracted, retaining the second disk 30 within the catheter, until the first disk engages the distal side of the septum S as depicted in FIG. 9. Since the disk is significantly larger than the defect, i.e., preferably at least 1.6 times the size of the defect, the frame will engage the septum and may not readily be drawn through the defect.

The second disk 30 may then be urged out of the distal end of the catheter on the proximal side of the defect. This may be accomplished by any number of means, such as by urging the disk with a plunger, as explained below. In another embodiment the catheter is simply retracted proximally. The first disk 20 will engage the distal side of the defect and, because the membranes 22,32 of the two disks are attached to one another to define the central conjoint disk, the second disk will be drawn out of the catheter as it is retracted. This will also ensure that the second disk is deployed on the side of the septum opposite the first disk because the second disk will not be pulled out of the catheter until after the first disk firmly engages the opposite side of the septum.

The resilient frame 34 of the second disk will elastically substantially return to its initial, non-deformed shape and pull the membrane 32 taut upon exiting the catheter. In so doing, the second disk will be urged against the proximal wall of the septum, as shown in FIG. 10. This will also automatically position the central conjoint disk 40 within the defect as the conjoint disk serves to connect the first disk 20, which is disposed on one side of the septum, to the second disk 30, which is disposed on the other side of the septum.

Figure 11:
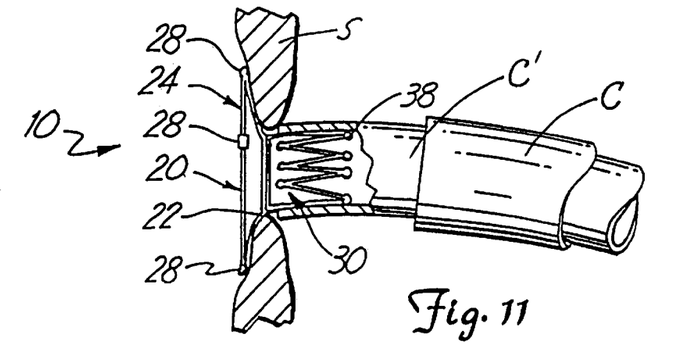
FIG. 11 is a view similar to FIG. 9, but depicts an alternative embodiment wherein a coaxial catheter delivery is employed.

In an alternative, preferred embodiment of the invention, shown in FIG. 11, a second delivery catheter C' is used. In this embodiment, the initial step in closing a septal defect is to position an outer guiding catheter adjacent the defect. Preferably, the guiding catheter is passed through the defect so that its distal tip is disposed on the distal side of the septum, and is desirably spaced some distance distally of the septum and toward the mid portion of the cardiac chamber.

A closure device of the invention may be positioned within the delivery catheter C' adjacent its distal end, substantially as shown in FIG. 8 with respect to the catheter C. The delivery catheter C' may then be passed coaxially through the guiding catheter C until it protrudes distally beyond the distal end of the guiding catheter. The first disk 20 of the closure device may then be urged out of the distal end of the catheter, substantially as described above with respect to the embodiment shown in FIGS. 8–10. The deployment of the second disk 30 of the closure device is substantially similar to the method outlined above. For instance, the guiding catheter and the delivery catheter may be retracted proximally together as a unit, with the two coaxial catheters acting substantially the same as the single catheter described above.

Alternatively, one may retract the guiding catheter at any time after the delivery catheter C' is positioned on the distal side of the septal defect. For instance, once the first disk 20 is deployed, the guiding catheter C may be retracted to a position spaced proximally well away from the septal defect. The delivery catheter C' may then be individually retracted through the guiding catheter to deploy the second disk 30 rather than moving the guiding catheter and delivery catheter together as a unit.

Because the closure device of the invention is mechanically much simpler than prior art designs, the method of deploying it to occlude a defect is also much simpler. Whereas prior art devices require a great deal of remote manipulation in order to deploy and attach an umbrella to the septum, deployment of the present device 10 is quite easy. Because the resilient frames 24,34 automatically expand to the desired configuration and position the conjoint disk 40 within a defect, there is no need for a series of cables or the like to remotely deploy a complex arrangement of separate elements, such as a number of different radial arms.

Furthermore, the present invention can be used to treat patients untreatable with prior art devices. The cumbersome mechanical devices taught by others cannot be delivered through a small catheter because they are too large and bulky to fit through such catheters; prior art systems have generally been limited to use with 11 French (about 3.7 mm) or larger catheters. Also, since they are composed of relatively rigid parts, such as radial umbrella arms, they cannot follow very tortuous paths. Because of its compact, collapsible design, a closure device 10 of the invention may readily be used with 6 to 8 French (2.0 mm) catheters. The flexibility of the frames 24,34 also permits the device to follow a catheter through fairly tortuous paths. The reduction in the size of the delivery system allows a closure device of invention to be utilized to treat small children, e.g., under 8 kilograms, which were simply untreatable with most prior art devices.

FIGS. 13–16 depict a preferred embodiment of a delivery system for delivering a closure device of the invention. The system generally includes a handle 210 for remotely manipulating the delivery system and a distal section 208 for urging the closure device into its desired position.

Figure 13:
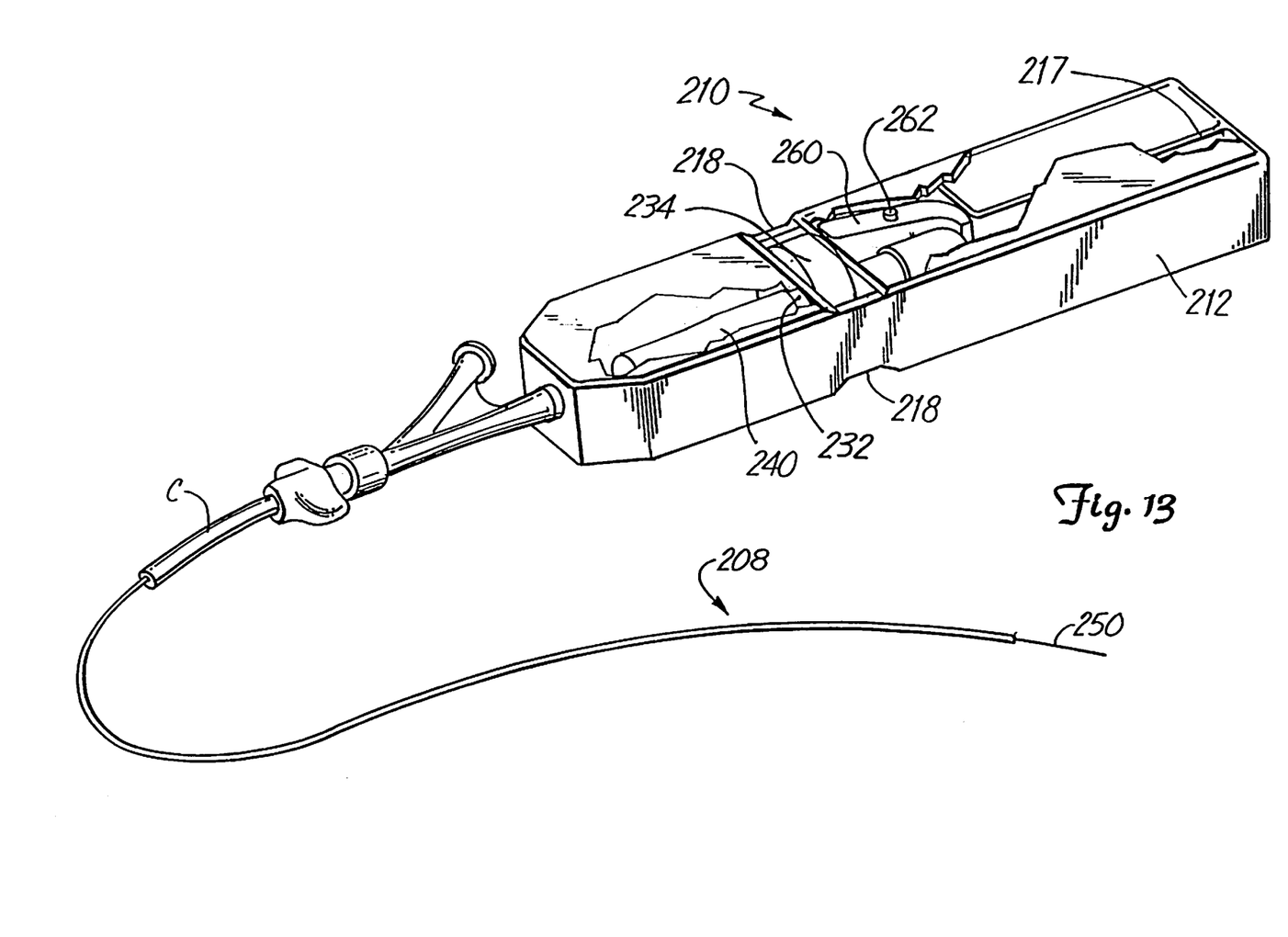
FIG. 13 is a perspective view of a handle of a delivery system for delivering a device of the invention.
Figure 14:
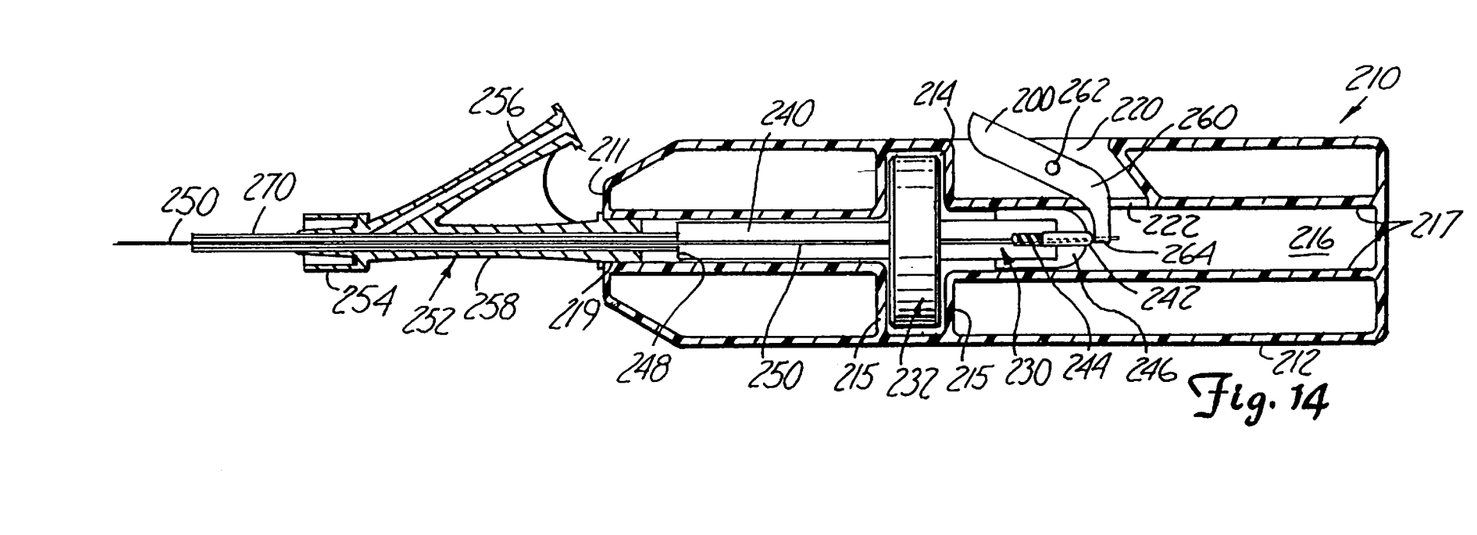
FIG. 14 is a schematic view of the handle for the delivery system shown in FIG. 13.

Referring first to FIGS. 13 and 14, the handle 210 includes a manually graspable housing 212. Although the housing may be of any desired size and shape, it is desirably generally rectangular in cross section and sized to be readily grasped with one hand by the surgeon during operation. The housing 212 is preferably elongate so that it may substantially enclose the control mechanism 230 of the delivery system. The housing may include a first chamber 214 and a second chamber 216, with the first chamber being oriented generally perpendicularly to the second chamber. The first chamber 214 is adapted to receive a rotor 232 of the control mechanism and includes laterally extending walls 215 which are adapted to serve as stops for the rotor. As explained in more detail below, as the rotor is turned, it will urge a central member 270 to slide within the second chamber 216. The walls 215 of the first chamber serve as stops to prevent movement of the rotor with the central member along the length of the handle.

The first chamber 214 may also be associated with a detent or detents 218 formed on the outer surface of the handle. (These detents are best seen in FIG. 13.) Each detent may be substantially as wide as the first chamber 214 and extend inwardly of the exterior of the housing 212. The rotor 232 is sized so that its outer surface 234 protrudes outwardly of the housing 212 through these detents 218. In this manner, an operator may manually grasp and rotate the rotor by accessing the outer surface 234 of the rotor through the detents 218.

By having the detents recessed below the outer surface of the housing 212, the outer surface of the rotor 234 may be readily accessible through the detents, yet not extend appreciably beyond the exterior of the rest of the handle. This permits the operator to readily manipulate the rotor, yet minimizes the risk that the rotor will be inadvertently turned through unintended contact. Although one detent on a single face of the housing may suffice, it is preferred that two detents be used, with one detent being positioned on each of two opposing faces of the housing, as shown in FIG. 13. If so desired, the outer surface 234 of the rotor may be textured, as shown, in order to make the rotor easier to grasp when the operator is wearing surgical gloves or the like.

The second chamber 216 is elongate and desirably extends generally along the center of the handle. The second chamber 216 may extend along substantially the entire length of the handle (as shown), but need not do so. The second chamber 216 must extend through the distal end 211 of the housing to define a distal port 219 therein, though, to permit communication of the control means 230 with the catheter C. The second chamber may be defined by a pair of generally parallel, spaced apart walls 217 which define a chamber sufficiently wide enough for the central member 240 of the control mechanism 230 to slide axially therein without undue friction. However, it is preferred that the walls 217 be spaced only slightly away from the central member 240 to limit lateral movement of the central member within the housing.

The housing 212 of the handle may also include a recess 220 for receiving a release lever 260. The recess is desirably sized so that it may substantially entirely enclose the release lever when the control mechanism is in its fully retracted position, i.e., before either of the disks of the device have been deployed, as explained in more detail below. The recess also includes a notch 222 which extends through a sidewall 217 of the first chamber. This notch is provided so that an end 264 of the release lever may pass therethrough for operative connection to the connecting rod 242. The notch 222 should be sized to permit the release lever to be moved about pivot pin 262 in order to deploy the closure device of the invention. By providing a recess which substantially encloses the release lever 260 before the closure device has been deployed, the chance of inadvertent release of the closure device before it is in its desired position is minimized.

As noted above, the rotor 232 and the central member 240 of the control mechanism are operatively connected to one another through a threaded engagement. The central member 240 is desirably generally cylindrical in shape and is externally threaded with screw-type threads extending along a significant portion of its length; if so desired, the screw threads may extend along substantially the entire length of the central member. The rotor 232 is provided with internal threads (not shown) which mate with the external threads on the central member. Thus, by rotating the rotor within the first chamber 214, one can induce axial movement of the central member within the second chamber 216. Furthermore, if the pitch of the threads on the rotor and the central member are known, the precise distance which the central member moves for a given angle of rotation of the rotor can be readily determined. This permits precise control of movement of the central member without any unnecessarily complex mechanical structure.

The generally cylindrical central member includes a bore (not shown) which extends along its entire length. This bore is located generally along the axis of the cylindrical central member and is sized to receive a core wire 250 which passes through the central member. The core wire may advantageously comprise a standard guide wire, as are known. In a preferred embodiment, the core wire is formed of a super-elastic material, such as NiTi alloy. The bore should be large enough to permit the central member to turn freely with respect to the core wire and to allow the core wire to slide axially within the central member.

The proximal end of the core wire 250 is operatively connected to an end 264 of the release lever 260. One preferred embodiment of such a connection, shown in FIG. 14, utilizes a connecting rod 242 which may be attached at its distal end to the proximal end of the core wire and at its proximal end to the end 264 of the release lever. Thus, by pivoting the release lever 260 about its pivot pin 262, one may draw the core wire axially within the bore in central member 240 in a proximal direction.

For reasons made more clear below, the release lever 260 is desirably biased in a clockwise direction in FIG. 14, i.e., such that the core wire 250 is generally urged in a distal direction. In the embodiment shown in FIG. 14, the release lever is so biased by means of a biasing spring 244. The biasing spring is a tension spring connected at a first end to the connecting rod 242 and at its opposite end to the central member 240. This urges the connecting rod in a distal direction, i.e., to the right in FIG. 14, to thereby bias the release lever in a clockwise direction.

If so desired, a cap 246 may be provided at the distal end of the central member 240. The cap includes a bore therethrough which is axially aligned with the axis of the central member to permit the connecting rod 242 to slide with respect to the cap in response to movement of the release lever 260. The cap 246 may extend distally along the sides of a proximal portion of the central member 240, as shown. The cap 246 is desirably formed of a machinable or moldable plastic; Delrin, which is available from DuPont, has been found to work well.

A generally tubular urging member 270 may be attached to the distal end 248 of the central member. The urging member 270 should be attached to the central member so that it may move axially as the central member is moved by rotation of the rotor 232. The axis of the urging member desirably generally coincides with the axis of the central member so that the core wire 250 may extend into and slide within the urging member, for reasons explained below.

The urging member and the core wire are received within a catheter C (see FIG. 13). The proximal end of the catheter is desirably attached to the distal end 211 of the housing. Although the catheter may be directly attached to the distal end of the housing, in the embodiment shown in FIGS. 13 and 14 an integrally formed side arm connector, as is commercially readily available, is used. This connector 252 is attached to the housing and is desirably in sealing engagement with the distal port 219 of the housing, such as by means of mating threads, as shown. The connector generally includes a first tubular member 258 which is generally axially aligned with the rest of the control mechanism, including the central member 240, and a second tube 256 which extends radially outwardly at an angle from the first tube 258. The second tube 256 may be used to introduce fluids into the catheter during deployment of the closure device; these fluids may include, for instance, isotonic saline (0.9%) to flush the lumen of the catheter prior to introduction to remove all air bubbles. The connector 252 may include any useful means for connecting the catheter C such that a generally fluid-tight seal is achieved. For instance, a luer lock 254, such as that shown, may be used. It is preferred that the catheter be joined to the handle in a manner which permits the catheter to be rotated or turned with respect to the handle.

Figure 15:
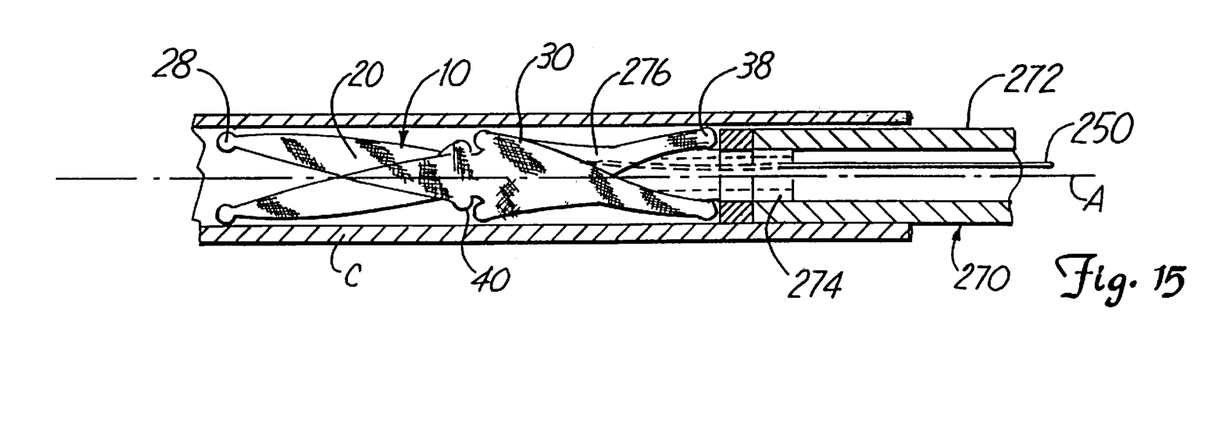
FIG. 15 is a schematic, cross-sectional view of the distal end of a delivery system for delivering a device of the invention.
Figure 16:
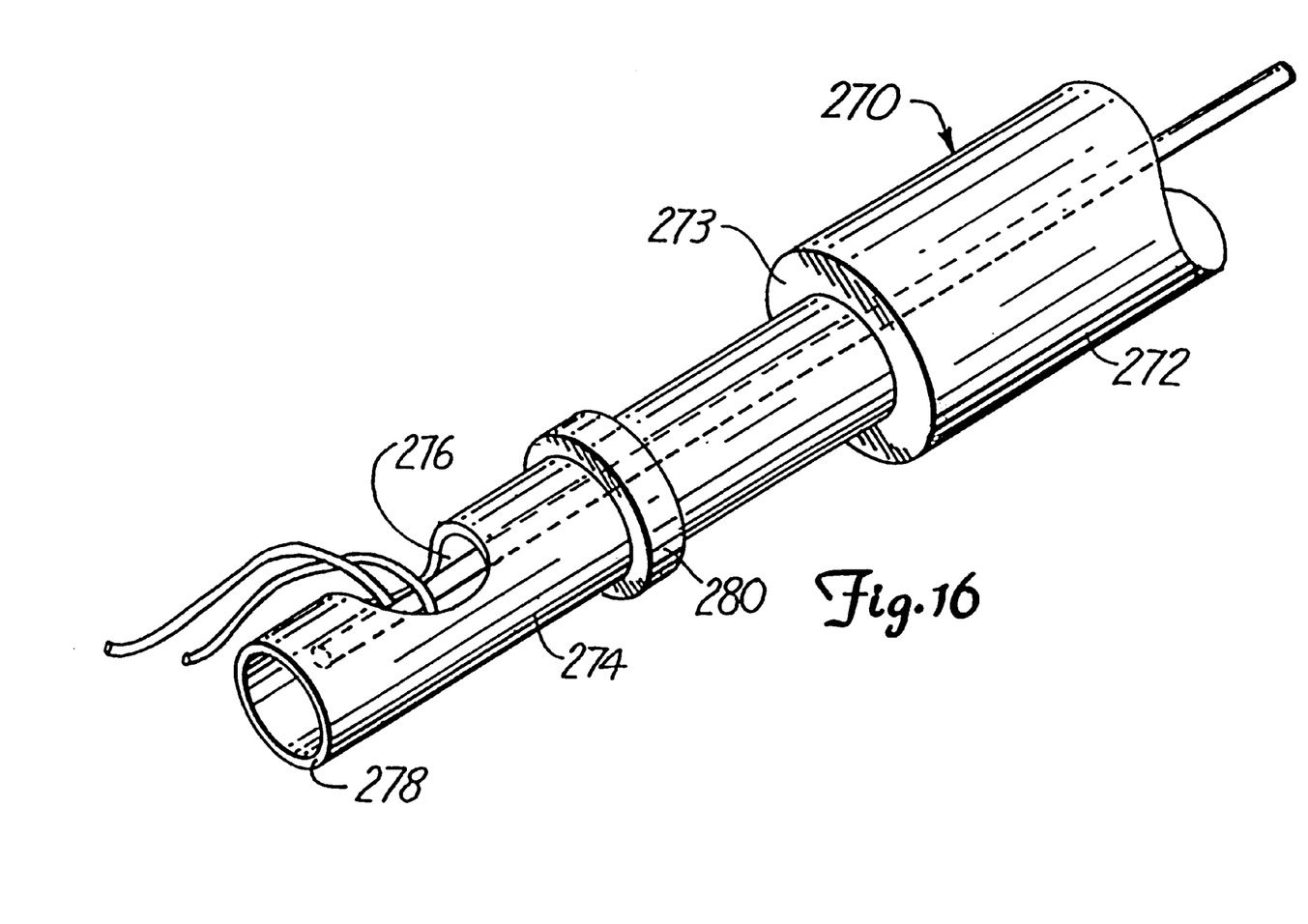
FIG. 16 is a perspective view of the distal portion of the delivery system shown in FIG. 15.

FIGS. 15 and 16 show a distal portion of a preferred embodiment of a delivery device of the invention. The core wire 250 extends within the urging member 270 to a position adjacent the distal end of the urging member. Although the core wire 250 may remain substantially along the axis of the urging member, as best seen in FIG. 15 it is generally preferred that the core wire be displaced slightly from that axis A.

The majority of the length of the urging member 270 comprises a flexible tube 272, which may be substantially similar to catheters such as are commonly known. The flexible tube should be sized to permit the core wire 250 to move freely therewithin, yet permit the urging member to be guided through the catheter C along its length for deployment of the closure device 10. The final distal segment of the urging member comprises a short tube 274 which is formed of a stiffer material, such as a metal such as surgical stainless steel or the like. This metal tube 274 may be attached to the flexible tube 272 by any known means. For instance, a length of the tube 274 may be received within the distal end of the flexible tube 272 and may be held in place by means of a biologically compatible cementitious material or even a mere friction fit.

As best seen in FIG. 15, the distal end 278 of the metal tube is adapted to contact a closure device 10 of the invention, such as at the conjoint disk 40, as shown. Thus, by moving the urging member 270 distally, i.e., to the left in FIG. 15, one may urge the closure device toward the distal end of the catheter. The metal tube 274 should therefore be relatively small in its outer diameter so that the second disk 30 of the closure device may be wrapped about the tube for deployment. This metal tube 274 may, for instance, have a length of about 10–20 mm and an outer diameter on the order of about 2 mm or less. The flexible tube 272 is desirably larger in outer diameter than the metal tube 274. This presents a forward shoulder 273 on the flexible tube which may engage the disk 30 to further urge it along the catheter.

If so desired, a relatively small, thin band 280 may be placed about the metal tube 274. This band 280 is desirably sized to space the metal tube from the wall of the catheter C as the metal tube is moved within the lumen of the catheter. This band may be formed of any suitable material and may simply be placed about an attached to the metal tube. In a preferred embodiment, though, the band 280 is integrally formed with the metal tube, simply comprising a generally annular projection extending outwardly of the generally cylindrical metal tube.

This preferred embodiment of a delivery system may be used substantially as described above to deploy a closure device 10 of the invention. The urging member 270 is used to urge the closure device along the lumen of the catheter until it is positioned adjacent the distal end of the catheter; as explained in more detail above, the distal end of the catheter may be positioned on the distal side of the defect prior to deployment of the first disk 20. Once the catheter is properly positioned, the first disk may be urged distally out of the catheter within the present device by turning the rotor 232 with respect to the housing 212 of the handle. As noted above, since the pitch of the threads on the central member 240 and the rotor 232 are known, by turning the rotor through a predetermined angle or number of revolutions, the central member may be urged distally by a fixed distance. This in turn forces the urging member 270 to move distally, urging the closure device 10 out of the distal end of the catheter. The control mechanism 230 of the delivery system therefore permits one to urge the first disk 20 out of the catheter without risking deploying the second disk 30 of the closure device on the distal side of the septum S by urging the closure device too far along the catheter. The second disk may be deployed on the distal side of the septal defect substantially as described above.

One additional aspect of the present delivery system is that it permits the closure device 10 to be securely held until it is properly deployed to prevent accidental release. In a preferred embodiment, a tether (290 in FIG. 16) is attached to the closure device. This tether desirably defines a loop, as shown, and may be attached to any part of the closure device, although attaching the tether to the conjoint disk 40 is generally preferred. The metal tube 274 is provided with an opening 276 in its side which permits access to the core wire 250. During deployment, the core wire 250 passes through a segment of the loop defined by the tether 290 to hold it in place. The core wire desirably extends distally beyond the opening 276 to prevent the tether from being inadvertently slipped over the end of the core wire, thereby releasing the closure device.

When the closure device has been properly deployed with one disk on either side of the defect, the tether may be released from the delivery system. Manually pressing on the flange 266 of the release lever 260 will cause the release lever to pivot in a generally counterclockwise direction in FIG. 14. This in turn draws the core wire 250 generally axially in a proximal direction, as explained above. The distance which the full rotation of the release lever about its pivot pin imparts to the core wire should be sufficient to draw the core wire proximally behind the distal edge of the opening 276 in the metal tube, and desirably is sufficient to draw the core wire substantially behind the opening so that a rearward portion of the opening may draw the tether off of the core wire. This permits the tether 290 to slip off the core wire 250, completing deployment of the closure device.

It should be noted that when the central member is in its initial position before either disk has been deployed, the release lever 260 desirably is received substantially entirely within the recess 220 in the handle. Only when the central member is moved distally to deploy the closure device will the release lever be moved so that it may project outwardly of the handle. This will prevent the inadvertent depression of the release lever before the closure device has been deployed.

In an alternative embodiment (not shown), a slightly different means of releasing the tether 290 is used. Rather than using a core wire which is simply passed through the loop defined by the tether, the tether may actually be severed. The metal tube 274 may have a small hole drilled diametrically therethrough. The tether may be passed through this hole and be tied into a knot at its end. The core wire 250 in this variant (not shown) is disposed proximally of the tether, and has a sharpened edge at its distal end. When the device is to be released, the core wire is urged distally by the release mechanism (instead of being drawn proximally as in the previous embodiment). The sharpened distal edge of the core wire then cuts the tether in a manner akin to a guillotine, releasing the device.

Although the foregoing has focused on application of the present invention to occlude atrial septal defects, the invention is not limited to occluding such defects. For instance, the instant closure device can be used to treat ventricular septal defects, patent ductus arteriosus or any other congenital or acquired orificial or tubular communications between vascular chambers or vessels.

While a preferred embodiment of the present invention has been described, it should be understood that various changes, adaptations and modifications may be made therein without departing from the spirit of the invention and the scope of the appended claims.

What is claimed is:

1. A septal defect closure device comprising a first member and a second member each comprising a self-expanding structure exhibiting a spring-like behavioural component for moving the member between a compressed orientation for passage through a medical instrument having an inner diameter and an expanded orientation having an enlarged diameter for tautly holding at least a portion of the closure device against a septum, the enlarged diameter of the member being greater than the inner diameter of the medical instrument; each of the first and second members also including a central portion, at least a substantial portion of the central portion of the first member being in communication with at least a substantial portion of the central portion of the first member.

2. The device of claim 1, wherein the portions of the disks in communication with one another are attached to one another to define a conjoint disk.

3. The device of claim 2, wherein a maximum dimension of at least one of the first and second members is between about 1.6 and about 2.5 times a diameter of the conjoint disk.

4. The device of claim 1, wherein the first member in its compressed orientation extends primarily distally from the second member and the second member in its compressed orientation extends primarily proximally from the first member, each member in its expanded orientation extending primarily radially outward from its central portion.

5. The device of claim 1, wherein each of the first and second members comprises a flexible fabric disk.

6. The device of claim 1 wherein said at least a substantial portion of the central portion of said first and second members includes said central portions of said first and second disk members, respectively.

* * * * *

UNITED STATES PATENT AND TRADEMARK OFFICE
CERTIFICATE OF CORRECTION

PATENT NO.   : 6,077,281
DATED        : June 20, 2000
INVENTOR(S)  : Gladwin S. Das It is certified that error appears in the above-identified patent and that said Letters Patent is hereby corrected as shown below:

<u>Column 18,</u>
Line 24, delete "first" and insert -- second --.

Signed and Sealed this

Twenty-fourth Day of December, 2002

JAMES E. ROGAN
*Director of the United States Patent and Trademark Office*